(12) United States Patent
Yan

(10) Patent No.: US 12,714,794 B2
(45) Date of Patent: Aug. 25, 2026

(54) NEEDLELESS SKIN DEEP FILLER INJECTION DEVICE

(71) Applicant: REVYOUTH.LTD, Nanchang (CN)

(72) Inventor: Yongxing Yan, Shanghai (CN)

(73) Assignee: REVYOUTH.LTD, Nanchang (CN)

( * ) Notice: Subject to any disclaimer, the term of this patent is extended or adjusted under 35 U.S.C. 154(b) by 595 days.

(21) Appl. No.: 18/035,752

(22) PCT Filed: Mar. 22, 2021

(86) PCT No.: PCT/CN2021/082039

§ 371 (c)(1),
(2) Date: May 8, 2023

(87) PCT Pub. No.: WO2022/198372

PCT Pub. Date: Sep. 29, 2022

(65) Prior Publication Data

US 2024/0009399 A1 Jan. 11, 2024

(51) Int. Cl.
*A61M 5/30* (2006.01)

(52) U.S. Cl.
CPC .................................... *A61M 5/30* (2013.01)

(58) Field of Classification Search
CPC .......... A61M 37/00; A61M 2037/0007; A61M 37/0076; A61M 37/0084; A61M 5/30; A61M 5/3007; A61M 37/0092; A61M 11/005; A61M 11/06
See application file for complete search history.

(56) References Cited

U.S. PATENT DOCUMENTS

| | | | | |
|---|---|---|---|---|
| 10,709,843 | B2 * | 7/2020 | Gamliel .................. | A61M 5/46 |
| 12,029,627 | B2 * | 7/2024 | Goldenberg ............. | A61D 7/00 |
| 2005/0013840 | A1 * | 1/2005 | Potter .............. | A61M 37/0069<br>424/422 |
| 2006/0258986 | A1 * | 11/2006 | Hunter .................. | A61M 5/20<br>604/164.01 |

(Continued)

FOREIGN PATENT DOCUMENTS

| | | |
|---|---|---|
| CN | 205598425 U | 9/2016 |
| CN | 206793984 U | 12/2017 |

(Continued)

*Primary Examiner* — Quynh-Nhu H. Vu
(74) *Attorney, Agent, or Firm* — Bayramoglu Law Offices LLC

(57) ABSTRACT

A needleless skin deep filler injection device includes: a gun body, where an accommodating cavity is provided in the gun body; an injection tube provided at a front end of the gun body and configured to store a to-be-injected liquid; an injection driving structure provided in the accommodating cavity, connected to the injection tube through a liquid pushing rod, and configured to inject the to-be-injected liquid in the injection tube; a negative-pressure freezing structure sleeved on a front end of the injection tube and configured to form a negative pressure between an injection port of the injection tube and a human skin for cooling; and a knock wall-breaking structure provided in the accommodating cavity, connected to a wall of the injection tube, and configured to transfer low-frequency vibration to the human skin through the injection tube and the negative-pressure freezing structure.

9 Claims, 3 Drawing Sheets

(56) References Cited

U.S. PATENT DOCUMENTS

| | | | | | |
|---|---|---|---|---|---|
| 2009/0299328 | A1 * | 12/2009 | Mudd | A61M 5/31575 | 604/60 |
| 2015/0045723 | A1 * | 2/2015 | Paithankar | A61P 17/10 | 604/22 |

FOREIGN PATENT DOCUMENTS

| | | | | |
|---|---|---|---|---|
| CN | 108744163 | A | 11/2018 | |
| CN | 110585586 | A | 12/2019 | |
| CN | 111097083 | A | 5/2020 | |
| CN | 210447780 | U | 5/2020 | |
| EP | 3662782 | A1 | 6/2020 | |
| WO | WO-2015021446 | A2 * | 2/2015 | A61P 17/10 |

* cited by examiner

NEEDLELESS SKIN DEEP FILLER INJECTION DEVICE

CROSS REFERENCE TO THE RELATED APPLICATIONS

This application is the national phase entry of International Application No. PCT/CN2021/082039, filed on Mar. 22, 2021, the entire contents of which are incorporated herein by reference.

TECHNICAL FIELD

The present disclosure relates to the technical field of needleless injection, and in particular to a needleless skin deep filler injection device.

BACKGROUND

Drugs, beauty products and the like are usually delivered to human bodies by either needle injection or needleless injection. Due to a high risk for skin damage in injection, needleless delivery is used in the beauty industry. Needleless injection is an injection method without the conventional capillary needle. Without piercing the body through the needle, it propels a liquid under a pressure of a needleless injection pusher, and dispersively injects the liquid into subcutaneous tissues of patients. To some extent, the needleless injection reduces pains and fears of the patients to pierce the body.

However, most of prior needleless injectors in the beauty industry are provided with only an injection structure for producing a high-pressure gas flow. They rarely realize precise quantitative injection, and cannot accurately lock and locate sites below dermis. This is averse to permeation of the liquid to affect the beauty effect. Moreover, the prior needleless injectors can only reduce pains of users to some extent, and cannot greatly relieve the injection pain, thereby affecting the user experience. Therefore, it is desired to develop a needleless skin deep filler injection device capable of relieving the injection pain desirably, accurately locking and locating sites under the dermis, and realizing the quantitative injection, so as to improve the beauty effect of the injected liquid and the user experience.

SUMMARY

An objective of the present disclosure is to provide a needleless skin deep filler injection device. The needleless skin deep filler injection device can relieve an injection pain desirably, can accurately lock and locate sites below dermis, and can facilitate permeation of the liquid to realize quantitative injection, thereby improving a beauty effect of the injected liquid and a user experience.

The present disclosure provides the following technical solutions.

The present disclosure provides a needleless skin deep filler injection device, including:

- a gun body, where an accommodating cavity is provided in the gun body;
- an injection tube provided at a front end of the gun body and configured to store a to-be-injected liquid;
- an injection driving structure provided in the accommodating cavity, connected to the injection tube through a liquid pushing rod, and configured to inject the to-be-injected liquid in the injection tube;
- a negative-pressure freezing structure sleeved on a front end of the injection tube and configured to form a negative pressure between an injection port of the injection tube and a human skin for cooling; and
- a knock wall-breaking structure provided in the accommodating cavity, connected to a wall of the injection tube, and configured to transfer low-frequency vibration to the human skin through the injection tube and the negative-pressure freezing structure.

With the injection tube at the front end of the gun body, and the injection driving structure in the accommodating cavity of the gun body, the to-be-injected liquid in the injection tube can be injected. With the negative-pressure freezing structure sleeved on the front end of the injection tube, a negative-pressure environment for cooling can be formed between the injection port and the human skin in injection to facilitate adsorption of the skin and injection of the liquid. Meanwhile, the low temperature can relieve an injection pain desirably and ensure user experience. Additionally, with the knock wall-breaking structure in the accommodating cavity, low-frequency vibration can be transferred to the human skin at a specific frequency before injection. This accurately locks and locates sites below dermis, and facilitates permeation of the liquid to realize quantitative injection of the liquid, thereby improving a beauty effect of the injected liquid.

Specifically, before the device is used, the to-be-injected liquid such as hyaluronic acid is injected into the injection tube. The negative-pressure freezing structure is sleeved on the front end of the injection tube, with a port attached to the human skin. Through the knock wall-breaking structure, the injection tube can be knocked for wall breaking. A negative pressure for cooling is formed between the injection port of the injection tube and the human skin through the negative-pressure freezing structure. At last, the to-be-injected liquid can be injected through the injection driving structure, thereby completing the needleless injection.

Further, the knock wall-breaking structure includes a first driving device fixed in the accommodating cavity;

- an output end of the first driving device is connected to a hammer body, and a vibrating member fixed on a sidewall of the accommodating cavity is provided at a side of the hammer body;
- a fixed member is provided between the gun body and the injection tube, and the fixed member is fixed on a front-end surface of the gun body; and
- when the first driving device works, the hammer body is pulled back and forth at a predetermined frequency, such that the hammer body knocks the vibrating member to transfer vibration to the human skin through the fixed member, the injection tube and the negative-pressure freezing structure.

Specifically, the output end of the first driving device is connected to the hammer body. The vibrating member fixed on the sidewall of the accommodating cavity is provided at the side of the hammer body. The fixed member is provided between the gun body and the injection tube. When the first driving device works, the hammer body can be pulled back and forth at the predetermined frequency, such that the hammer body continuously knocks the vibrating member to transfer the vibration to the human skin through the fixed member, the injection tube and the negative-pressure freezing structure.

Preferably, the first driving device is a cylinder in the embodiment. The cylinder drives the hammer body to perform a reciprocating motion at a frequency of 7 HZ to 10

HZ. In other embodiments, other similar driving devices and other driving frequencies can also be selected according to an actual condition.

Further, the injection driving structure includes a second driving device fixed in the accommodating cavity and located at a side of the first driving device;

an output end of the second driving device is connected to a threaded rod; a movable member is sleeved on the threaded rod; a fixed frame is provided outside the second driving device; and the movable member is slidably connected to the fixed frame, such that when the second driving device works, the movable member performs a reciprocating motion along the threaded rod; and a front end of the movable member is connected to a movable rod; and the movable rod runs through the vibrating member, a front-end sidewall of the gun body and the fixed member to be connected to the liquid pushing rod.

Specifically, the output end of the second driving device is connected to the threaded rod. The movable member is sleeved on the threaded rod. The fixed frame is provided outside the second driving device. The movable member is slidably connected to the fixed frame, such that when the second driving device works, the movable member performs the reciprocating motion along the threaded rod. The front end of the movable member is connected to the movable rod. The movable rod runs through the vibrating member, the front-end sidewall of the gun body and the fixed member to be connected to the liquid pushing rod. Therefore, the movable member in the reciprocating motion can drive the liquid pushing rod to perform a reciprocating motion, thereby injecting the to-be-injected liquid.

Preferably, the first driving device is a stepping motor in the embodiment. In other embodiments, other similar driving devices can also be selected according to an actual condition.

Further, an end of the fixed frame is connected to a limiting piece, and an end of the threaded rod is movably connected to the limiting piece; and an end of the movable rod is provided with a bending portion, and the bending portion bypasses the limiting piece.

Since the end of the fixed frame is connected to the limiting piece, and the end of the threaded rod is movably connected to the limiting piece, the motion of the movable member can be limited without affecting rotation of the threaded rod. The end of the movable rod is provided with the bending portion, and the bending portion bypasses the limiting piece, such that the motion of the movable rod can further be limited by the limiting piece.

Further, a through hole corresponding to the movable rod is formed in each of a side of the vibrating member, the front-end sidewall of the gun body, and a side of the fixed member.

Further, the negative-pressure freezing structure includes an annular main body, and the annular main body is sleeved on the front end of the injection tube; and a sealing ring connected to the annular main body is provided outside the injection tube.

The negative-pressure freezing structure is annular, and the sealing ring connected to the annular main body is provided outside the injection tube, which can facilitate installation and detachment of the negative-pressure freezing structure, as well as sealing between the injection tube and the negative-pressure freezing structure.

Further, a gas connector is provided at a side of the annular main body; and a negative pressure port communicated with an internal cavity of the annular main body is provided on the gas connector; and the negative pressure port is configured to connect a gas pump, such that when the annular main body contacts the human skin, the negative pressure is formed between the injection tube and the human skin.

The gas connector is provided at the side of the annular main body. The negative pressure port communicated with the internal cavity of the annular main body is provided on the gas connector. The negative pressure port is connected to the gas pump. When the annular main body contacts the human skin, and the gas pump works, the negative pressure is formed between the injection tube and the human skin to facilitate accurate quantitative injection of the to-be-injected liquid.

Preferably, a negative pressure of −5 Kpa to 50 Kpa is selected in the embodiment. In other embodiments, the negative pressure can be adjusted according to specific requirements.

Further, a first water connector and a second water connector are further provided at a side of the annular main body;

a water inlet and a water outlet are respectively formed in the first water connector and the second water connector; and an internal tubing connecting the water inlet and the water outlet is provided in a sidewall of the annular main body, such that frozen water entering the annular main body through the water inlet is drained from the water outlet through the internal tubing.

The first water connector and the second water connector are provided at the side of the annular main body. The water inlet and the water outlet are respectively formed in the first water connector and the second water connector. The internal tubing connecting the water inlet and the water outlet is provided in the sidewall of the annular main body. Therefore, water frozen by an electronic refrigerator and injected into the water inlet through a water pump can be drained from the water outlet through the internal tubing, thereby realizing refrigeration. This better reduces the pain in injection.

Preferably, a temperature of the annular main body is kept in a range of 5° C. to 15° C. through circulating water in the embodiment. In other embodiments, the temperature can be adjusted according to requirements in use.

Further, the injection tube is a transparent tube, and an end of the liquid pushing rod is provided with a barrel sealing ring tightly connected to the injection tube.

The injection tube is the transparent tube, such that a liquid volume in the injection tube can be observed conveniently and supplemented timely. In addition, a graduation line and the like may further be provided on a surface of the transparent tube, so as to measure the liquid volume in the injection tube more accurately. The end of the liquid pushing rod is provided with the barrel sealing ring tightly connected to the injection tube, such that the to-be-injected liquid can be injected conveniently without leakage.

Further, a bottom of the gun body is provided with a handle.

With the handle, a grip and the like at the bottom of the gun body, the injection device can be held and used conveniently.

According to the needleless skin deep filler injection device provided by the present disclosure, with the injection tube at the front end of the gun body, and the injection driving structure in the accommodating cavity of the gun body, the to-be-injected liquid in the injection tube can be injected. With the negative-pressure freezing structure sleeved on the front end of the injection tube, a negative-pressure environment for cooling can be formed between the injection port and the human skin in injection to facilitate adsorption of the skin and injection of the liquid. Meanwhile, the low temperature can relieve an injection pain desirably and ensure user experience. Additionally, with the knock wall-breaking structure in the accommodating cavity, low-frequency vibration can be transferred to the human skin at a specific frequency before injection. This accurately locks and locates sites below dermis, and facilitates permeation of the liquid to realize quantitative injection of the liquid, thereby improving a beauty effect of the injected liquid.

BRIEF DESCRIPTION OF THE DRAWINGS

Preferred implementations will be described below in a clear and easy-to-understand manner in conjunction with the drawings to further illustrate the above-mentioned characteristics, technical features, advantages, and implementation methods of the present disclosure.

In the figures: 10—gun body, 11—accommodating cavity, 12—handle, 20—injection tube, 21—barrel sealing ring, 31—liquid pushing rod, 32—second driving device, 33—threaded rod, 34—movable member, 35—fixed frame, 36—movable rod, 37—limiting piece, 41—first driving device, 42—hammer body, 43—vibrating member, 44—fixed member, 50—negative-pressure freezing structure, 51—annular main body, 52—sealing ring, 53—gas connector, 54—negative pressure port, 55—first water connector, 56—second water connector, 57—water inlet, and 58—water outlet.

DETAILED DESCRIPTION OF THE EMBODIMENTS

In order to explain the embodiments of the present disclosure or the technical solutions in the prior art more clearly, the specific implementations of the present disclosure will be described below with reference to the drawings. Apparently, the drawings in the following description show merely some embodiments of the present disclosure, and other drawings and other implementations may be derived from these drawings by those of ordinary skill in the art without creative efforts.

In order to keep the drawings concise, only components related to the present disclosure are schematically illustrated in each drawing, which do not represent its actual structure as a product. Further, for the purpose of a better understanding, only one of components having the same structure or function is schematically shown or marked in some drawings. In the description of the present disclosure, "one" not only means "only one", but also means "more than one".

Embodiment 1

Figure 1:
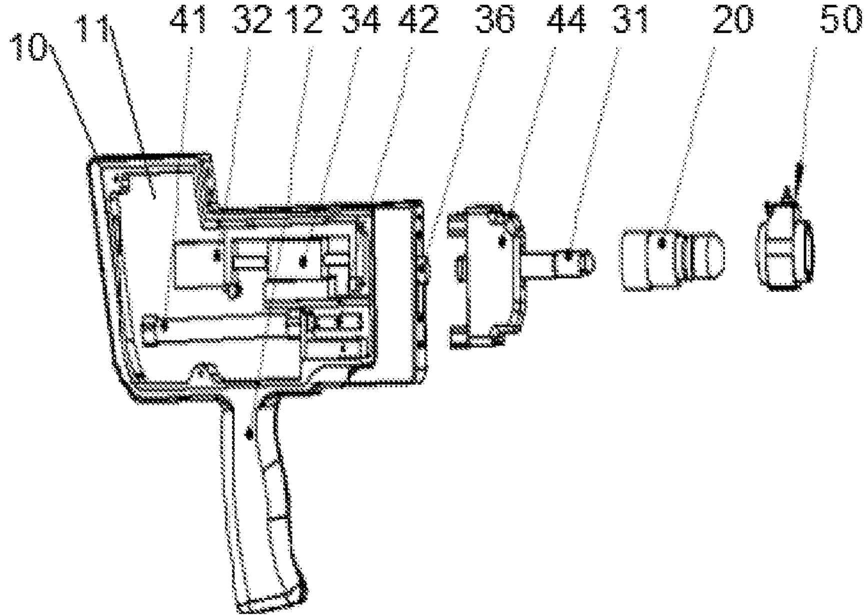
FIG. 1 is an overall structural schematic view according to an embodiment of the present disclosure.

According to an embodiment of the present disclosure, as shown in FIG. 1, the present disclosure provides a needleless skin deep filler injection device, including gun body 10, injection tube 20, an injection driving structure, negative-pressure freezing structure 50, and a knock wall-breaking structure.

Accommodating cavity 11 is provided in the gun body 10. The injection tube 20 is provided at a front end of the gun body 10 and configured to store a to-be-injected liquid.

Preferably, a bottom of the gun body 10 is provided with handle 12.

With the handle, a grip and the like at the bottom of the gun body 10, the injection device can be held and used conveniently.

The injection driving structure is provided in the accommodating cavity 11, connected to the injection tube 20 through liquid pushing rod 31, and configured to inject the to-be-injected liquid in the injection tube 20.

The negative-pressure freezing structure 50 is sleeved on a front end of the injection tube 20 and configured to form a negative pressure between an injection port of the injection tube 20 and a human skin for cooling.

The knock wall-breaking structure is provided in the accommodating cavity 11, connected to a wall of the injection tube 20, and configured to transfer low-frequency vibration to the human skin through the injection tube 20 and the negative-pressure freezing structure 50.

With the injection tube 20 at the front end of the gun body 10, and the injection driving structure in the accommodating cavity 11 of the gun body 10, the to-be-injected liquid in the injection tube 20 can be injected. With the negative-pressure freezing structure sleeved on the front end of the injection tube 20, a negative-pressure environment for cooling can be formed between the injection port and the human skin in injection to facilitate adsorption of the skin and injection of the liquid. Meanwhile, the low temperature can relieve an injection pain desirably and ensure user experience. Additionally, with the knock wall-breaking structure in the accommodating cavity 11, low-frequency vibration can be transferred to the human skin at a specific frequency before injection. This accurately locks and locates sites under dermis, and facilitates permeation of the liquid to realize quantitative injection of the liquid, thereby improving a beauty effect of the injected liquid.

Specifically, before the device is used, the to-be-injected liquid such as hyaluronic acid is injected into the injection tube 20. The negative-pressure freezing structure is sleeved on the front end of the injection tube 20, with a port attached to the human skin. Through the knock wall-breaking structure, the injection tube can be knocked for wall breaking. A negative pressure for cooling is formed between the injection port of the injection tube 20 and the human skin through the negative-pressure freezing structure. At last, the to-be-injected liquid can be injected through the injection driving structure, thereby completing the needleless injection.

Embodiment 2

Figure 2:
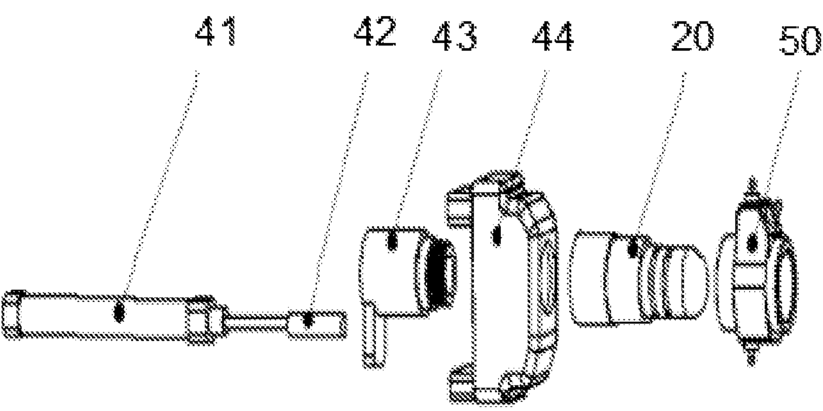
FIG. 2 is a schematic view of a knock wall-breaking structure according to an embodiment of the present disclosure.
Figure 5:
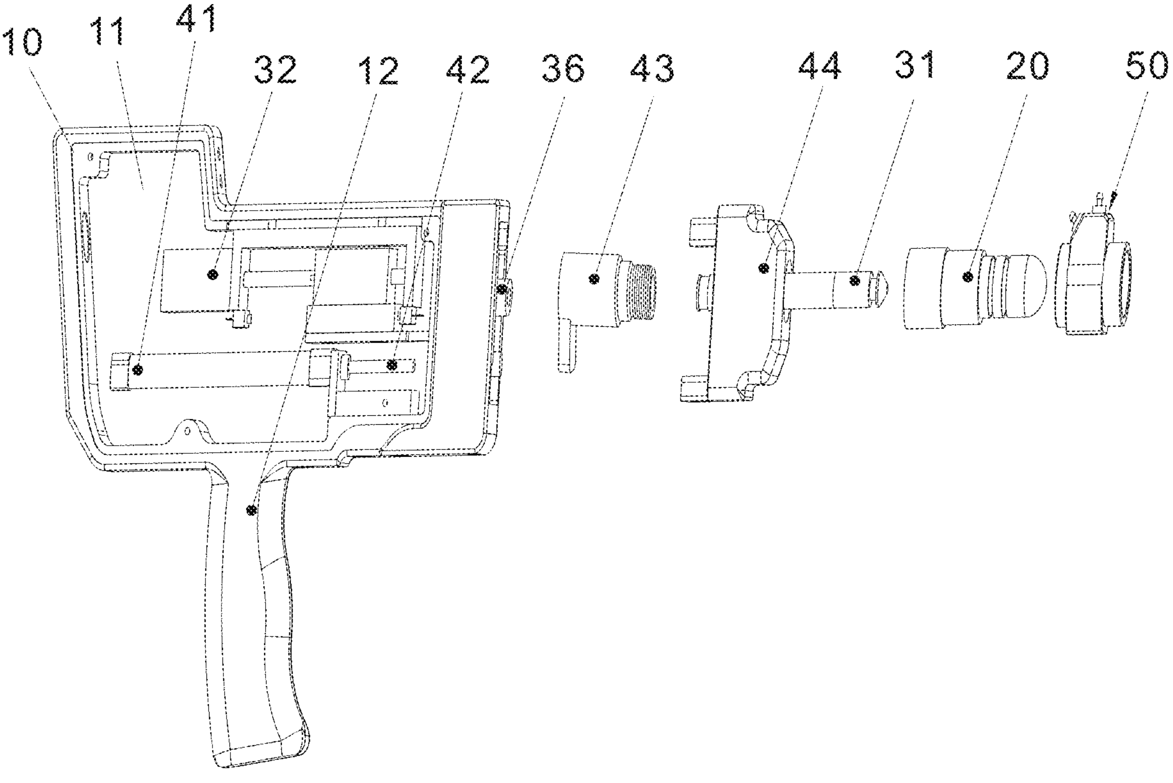
FIG. 5 is an overall structural schematic view according to an embodiment of the present disclosure including a knock wall-breaking structure.

According to an embodiment of the present disclosure, as shown in FIG. 1, FIG. 2 and FIG. 5, on the basis of Embodiment 1, the knock wall-breaking structure includes first driving device 41 fixed in the accommodating cavity 11. An output end of the first driving device 41 is connected to hammer body 42. Vibrating member 43 fixed on a sidewall of the accommodating cavity 11 is provided at a side of the hammer body 42.

Fixed member 44 is provided between the gun body 10 and the injection tube 20. The fixed member 44 is fixed on a front-end surface of the gun body 10. When the first driving device 41 works, the hammer body 42 is pulled back and forth at a predetermined frequency, such that the hammer body 42 knocks the vibrating member 43 to transfer vibration to the human skin through the fixed member 44, the injection tube 20 and the negative-pressure freezing structure.

Specifically, the output end of the first driving device 41 is connected to the hammer body 42. The vibrating member 43 fixed on the sidewall of the accommodating cavity 11 is provided at the side of the hammer body 42. The fixed member 44 is provided between the gun body 10 and the injection tube 20. When the first driving device 41 works, the hammer body 42 can be pulled back and forth at the predetermined frequency, such that the hammer body 42 continuously knocks the vibrating member 43 to transfer the vibration to the human skin through the fixed member 44, the injection tube 20 and the negative-pressure freezing structure.

Preferably, the first driving device 41 is a cylinder in the embodiment. The cylinder drives the hammer body 42 to perform a reciprocating motion at a frequency of 7 HZ to 10 HZ. In other embodiments, other similar driving devices and other driving frequencies can also be selected according to an actual condition.

Embodiment 3

Figure 3:
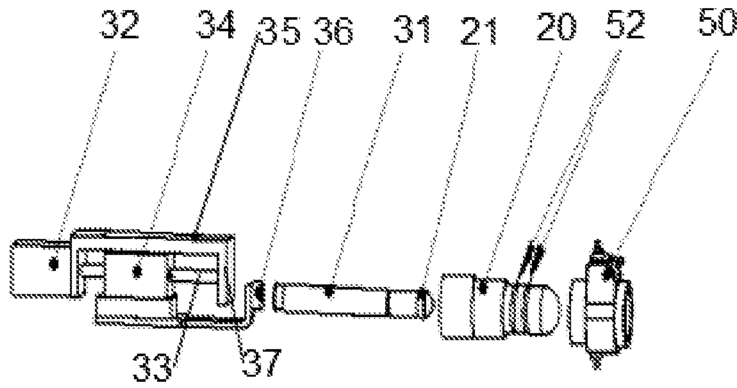
FIG. 3 is a schematic view of an injection driving structure according to an embodiment of the present disclosure.

According to an embodiment of the present disclosure, as shown in FIG. 1 and FIG. 3, on the basis of Embodiment 2, the injection driving structure includes second driving device 32 fixed in the accommodating cavity 11 and located at a side of the first driving device 41.

An output end of the second driving device 32 is connected to threaded rod 33. Movable member 34 is sleeved on the threaded rod 33. Fixed frame 35 is provided outside the second driving device 32. The movable member 34 is slidably connected to the fixed frame 35, such that when the second driving device 32 works, the movable member 34 performs a reciprocating motion along the threaded rod 33.

A front end of the movable member 34 is connected to movable rod 36. The movable rod 36 runs through the vibrating member 43, a front-end sidewall of the gun body 10 and the fixed member 44 to be connected to the liquid pushing rod 31.

Preferably, a through hole corresponding to the movable rod 36 is formed in each of a side of the vibrating member 43, the front-end sidewall of the gun body 10, and a side of the fixed member 44.

Specifically, the output end of the second driving device 32 is connected to the threaded rod 33. The movable member 34 is sleeved on the threaded rod 33. The fixed frame 35 is provided outside the second driving device 32. The movable member 34 is slidably connected to the fixed frame 35, such that when the second driving device 32 works, the movable member 34 performs the reciprocating motion along the threaded rod 33. The front end of the movable member 34 is connected to the movable rod 36. The movable rod 36 runs through the vibrating member 43, the front-end sidewall of the gun body 10 and the fixed member 44 to be connected to the liquid pushing rod 31. Therefore, the movable member 34 in the reciprocating motion can drive the liquid pushing rod 31 to perform a reciprocating motion, thereby injecting the to-be-injected liquid.

Preferably, the first driving device 32 is a stepping motor in the embodiment. In other embodiments, other similar driving devices can also be selected according to an actual condition.

Preferably, an end of the fixed frame 35 is connected to limiting piece 37. An end of the threaded rod 33 is movably connected to the limiting piece 37. An end of the movable rod 36 is provided with a bending portion. The bending portion bypasses the limiting piece 37.

Since the end of the fixed frame 35 is connected to the limiting piece 37, and the end of the threaded rod 33 is movably connected to the limiting piece 37, the motion of the movable member 34 can be limited without affecting rotation of the threaded rod 33. The end of the movable rod 36 is provided with the bending portion, and the bending portion bypasses the limiting piece 37, such that the motion of the movable rod 36 can further be limited by the limiting piece 37.

Preferably, the injection tube 20 is a transparent tube. An end of the liquid pushing rod 31 is provided with barrel sealing ring 21 tightly connected to the injection tube 20.

The injection tube 20 is the transparent tube, such that a liquid volume in the injection tube 20 can be observed conveniently and supplemented timely. In addition, a graduation line and the like may further be provided on a surface of the transparent tube 20, so as to measure the liquid volume in the injection tube 20 more accurately. The end of the liquid pushing rod 31 is provided with the barrel sealing ring 21 tightly connected to the injection tube 20, such that the to-be-injected liquid can be injected conveniently without leakage.

Embodiment 4

Figure 4:
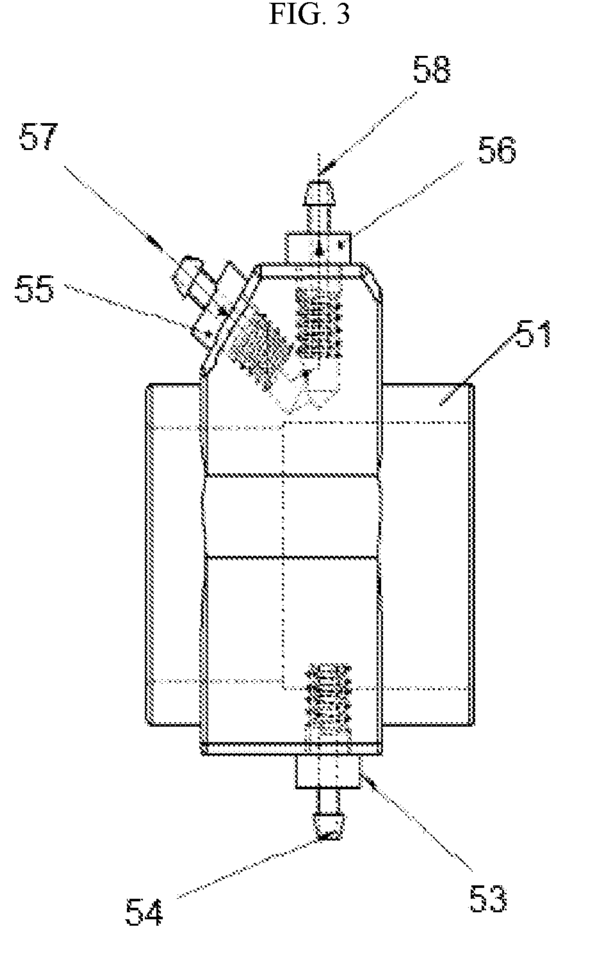
FIG. 4 is a schematic view of a negative-pressure freezing structure according to an embodiment of the present disclosure.

According to an embodiment of the present disclosure, as shown in FIG. 1 and FIG. 4, on the basis of any of the foregoing embodiments, the negative-pressure freezing structure 50 includes annular main body 51. The annular main body 51 is sleeved on the front end of the injection tube 20. Sealing ring 52 connected to the annular main body 51 is provided outside the injection tube 20.

The negative-pressure freezing structure 50 is annular, and the sealing ring 52 connected to the annular main body 51 is provided outside the injection tube 20, which can facilitate installation and detachment of the negative-pressure freezing structure 50, as well as sealing between the injection tube and the negative-pressure freezing structure.

Preferably, gas connector 53 is provided at a side of the annular main body 51. Negative pressure port 54 communicated with an internal cavity of the annular main body 51 is provided on the gas connector 53. The negative pressure port 54 is configured to connect a gas pump, such that when the annular main body 51 contacts the human skin, the negative pressure is formed between the injection tube 20 and the human skin.

The gas connector 53 is provided at the side of the annular main body 51. The negative pressure port 54 communicated with the internal cavity of the annular main body 51 is provided on the gas connector 53. The negative pressure port 54 is connected to the gas pump. When the annular main body 51 contacts the human skin, and the gas pump works, the negative pressure is formed between the injection tube 20 and the human skin to facilitate accurate quantitative injection of the to-be-injected liquid.

Preferably, a negative pressure of −5 Kpa to 50 Kpa is selected in the embodiment. In other embodiments, the negative pressure can be adjusted according to specific requirements.

Further preferably, first water connector 55 and second water connector 56 are further provided at a side of the annular main body 51. Water inlet 57 and water outlet 58 are respectively formed in the first water connector 55 and the second water connector 56. An internal tubing connecting the water inlet 57 and the water outlet 58 is provided in a sidewall of the annular main body 51, such that frozen water entering the annular main body 51 through the water inlet 57 is drained from the water outlet 58 through the internal tubing.

The first water connector 55 and the second water connector 56 are provided at the side of the annular main body 51. The water inlet 57 and the water outlet 58 are respectively formed in the first water connector 55 and the second water connector 56. The internal tubing connecting the water inlet 57 and the water outlet 58 is provided in the sidewall of the annular main body 51. Therefore, water frozen by an electronic refrigerator and injected into the water inlet 57 through a water pump can be drained from the water outlet 58 through the internal tubing, thereby realizing refrigeration. This better reduces the pain in injection.

Preferably, a temperature of the annular main body 51 is kept in a range of 5° C. to 15° C. through circulating water in the embodiment. In other embodiments, the temperature can be adjusted according to requirements in use.

It should be noted that the above embodiments can be freely combined as required. The above are merely preferred implementations of the present disclosure. It should be noted that several improvements and modifications may further be made by a person of ordinary skill in the art without departing from the principle of the present disclosure, and such improvements and modifications should also be deemed as falling within the protection scope of the present disclosure.

What is claimed is:

1. A needleless skin deep filler injection device, comprising:

a gun body, wherein an accommodating cavity is provided in the gun body;

an injection tube provided at a front end of the gun body and configured to store a to-be-injected liquid;

an injection driving structure provided in the accommodating cavity, connected to the injection tube through a liquid pushing rod, and configured to inject the to-be-injected liquid in the injection tube;

a negative-pressure freezing structure sleeved on a front end of the injection tube and configured to form a negative pressure between an injection port of the injection tube and a human skin for cooling; and a knock wall-breaking structure provided in the accommodating cavity, connected to a wall of the injection tube, and configured to transfer low-frequency vibration to the human skin through the injection tube and the negative-pressure freezing structure, wherein the knock wall-breaking structure comprises a first driving device fixed in the accommodating cavity; wherein an output end of the first driving device is connected to a hammer body, and a vibrating member fixed on a sidewall of the accommodating cavity is provided at a side of the hammer body;

a fixed member is provided between the gun body and the injection tube, and the fixed member is fixed on a front-end surface of the gun body; and when the first driving device works, the hammer body is pulled back and forth at a predetermined frequency, such that the hammer body knocks the vibrating member to transfer vibration to the human skin through the fixed member, the injection tube and the negative-pressure freezing structure.

2. The needleless skin deep filler injection device according to claim 1, wherein the injection driving structure comprises a second driving device fixed in the accommodating cavity and located at a side of the first driving device; wherein an output end of the second driving device is connected to a threaded rod; a movable member is sleeved on the threaded rod; a fixed frame is provided outside the second driving device; and the movable member is slidably connected to the fixed frame, such that when the second driving device works, the movable member performs a reciprocating motion along the threaded rod; and a front end of the movable member is connected to a movable rod; and the movable rod runs through the vibrating member, a front-end sidewall of the gun body and the fixed member to be connected to the liquid pushing rod.

3. The needleless skin deep filler injection device according to claim 2, wherein an end of the fixed frame is connected to a limiting piece, and an end of the threaded rod is movably connected to the limiting piece; and an end of the movable rod is provided with a bending portion, and the bending portion bypasses the limiting piece.

4. The needleless skin deep filler injection device according to claim 2, wherein a through hole corresponding to the movable rod is formed in each of a side of the vibrating member, the front-end sidewall of the gun body, and a side of the fixed member.

5. The needleless skin deep filler injection device according to claim 1, wherein the negative-pressure freezing structure comprises an annular main body, wherein the annular main body is sleeved on the front end of the injection tube; and a sealing ring connected to the annular main body is provided outside the injection tube.

6. The needleless skin deep filler injection device according to claim 5, wherein a gas connector is provided at a side of the annular main body; and a negative pressure port communicated with an internal cavity of the annular main body is provided on the gas connector; and the negative pressure port is configured to connect a gas pump, such that when the annular main body contacts the human skin, the negative pressure is formed between the injection tube and the human skin.

7. The needleless skin deep filler injection device according to claim 5, wherein a first water connector and a second water connector are further provided at a side of the annular main body;

a water inlet and a water outlet are respectively formed in the first water connector and the second water connector; and an internal tubing connecting the water inlet and the water outlet is provided in a sidewall of the annular main body, such that frozen water entering the annular main body through the water inlet is drained from the water outlet through the internal tubing.

8. The needleless skin deep filler injection device according to claim 1, wherein the injection tube is a transparent tube, and an end of the liquid pushing rod is provided with a barrel sealing ring tightly connected to the injection tube.

9. The needleless skin deep filler injection device according to claim 1, wherein a bottom of the gun body is provided with a handle.

* * * * *